United States Patent [19]

Favre

[11] 4,014,319
[45] Mar. 29, 1977

[54] INTERCRANIAL PRESSURE TRANSDUCER

[75] Inventor: Robert Favre, Lausanne, Switzerland

[73] Assignee: Etat de Vaud, Switzerland

[22] Filed: Feb. 28, 1975

[21] Appl. No.: 554,030

[30] Foreign Application Priority Data

Mar. 7, 1974 Switzerland .................. 3250/74

[52] U.S. Cl. .................. 128/2 R; 73/398 R; 73/393; 73/406; 128/2.05 E
[51] Int. Cl.$^2$ .................. A61B 5/00
[58] Field of Search ........... 128/2 P, 2 R, 2.05 D, 128/2.05 E, 2.1 A; 73/398 R, 406, 393

[56] References Cited

UNITED STATES PATENTS

| 3,034,356 | 5/1962 | Bieganski et al. | 128/2.05 E |
| 3,038,465 | 6/1962 | Allard et al. | 128/2.05 D |
| 3,727,463 | 4/1973 | Intraub | 73/398 R |
| 3,757,770 | 9/1973 | Brayshaw et al. | 128/2.05 D X |
| 3,853,117 | 12/1974 | Murr | 128/2.05 E X |

OTHER PUBLICATIONS

Atkinson; J. R., et al., *Journ. Of Neurosurgery*, 1967, vol. 27, No. 5, pp. 428–432.
Collins, C. C., *IEEE Trans. on Bio-Med. Engng.*, vol. BME-14, No. 2, Apr., 1967, pp. 74–83.

*Primary Examiner*—Kyle L. Howell
*Attorney, Agent, or Firm*—Robert E. Burns; Emmanuel J. Lobato; Bruce L. Adams

[57] ABSTRACT

The invention provides means for measuring the intercranial pressure of a patient. A small sealed capsule is located in a trephined hole in the patient's skull, with its active face in the form of a diaphragm in contact with the dura mater. The capsule includes a small hollow cylindrical permanent magnet slidable for a short distance along a smooth rod and held against a stop by the diaphragm with a pressure proportional to the intercranial pressure of the liquid within the skull. When an alternating magnetic field of sufficient intensity is applied to the magnet by an external wound inductor, it vibrates on and off its stop, producing an audible signal and the current in the inductor, at this point, is proportional to the said intercranial pressure.

10 Claims, 6 Drawing Figures

INTERCRANIAL PRESSURE TRANSDUCER

BACKGROUND OF THE INVENTION

The periodic measurement of intercranial pressure in patients over a long term presents great clinical interest. Various methods are known for measuring intercranial pressure all of which necessitate a connection with the atmosphere with an attendant risk of infection. Electronic transducers are known, but the life of the source of implanted energy is never more than ten days and the source is of relatively large dimensions.

SUMMARY OF THE INVENTION

The present invention has for its subject an intercranial pressure transducer of the passive type.

According to the present invention there is provided an intercranial pressure transducer of the passive type, including a capsule adapted to be housed in the thickness of the skull and containing a movable magnet and guide means enabling displacement of the said magnet, such that when the said magnet is submitted to a hydrostatic force generated by the pressure to be measured, and to a pulsed magnetic force opposed to the hydrostatic force and generated by the magnetic field of an external inductor, the said magnet makes an exteriorly perceptable movement when the said magnetic force becomes greater than the hydrostatic force.

BRIEF DESCRIPTION OF THE DRAWINGS

The accompanying drawings show three embodiments of a transducer in accordance with the invention, as well as one embodiment of an inductor.

DESCRIPTION OF THE PREFERRED EMBODIMENTS

Figure 1:
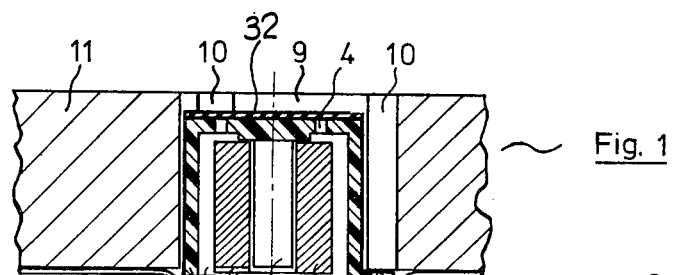
FIG. 1 shows an axial section of a transducer in accordance with a first embodiment, in use.

In the example of FIG. 1 a cylindrical magnet 1 is made of a material having a very high coercive force such as the alloy $SmCo_5$, with an axial hole. It surrounds a rod 3 made of ruby, along which it can be displaced freely. This assembly is housed in a capsule 2, closed on its operative face by an elastic diaphragm 5, made of mylar or rubber.

Variations of atmospheric pressure are transmitted to the interior of the capsule by the holes 4, which are covered with a silicone rubber sheet 32 which permits the passage of gases but not liquids.

Pneumatic damping of the movements of the magnet 1 by the air between the rod 3 and the diaphragm 5, is avoided by providing a transfer channel 6.

During implantation the implantation is housed in a trephined hole 9 made in the skull 11 and placed in such a manner that the film 5 lightly touches the dura mater 8 without substantially deforming it. To facilitate the operation, the transducer is provided with lugs 7 introduced into grooves 10 provided on the edges of the hole then slid between the dura mater 8 and the skull 11. The position of the transducer is thus determined by a mechanism similar to a bayonet fitting.

Figure 2:
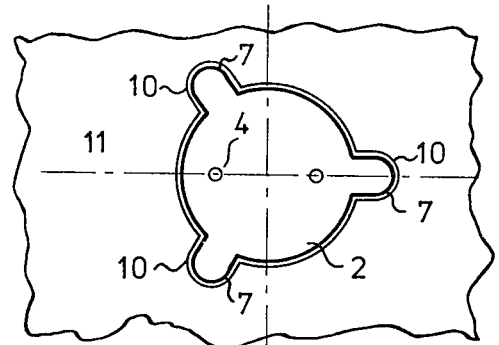
FIG. 2 is a plan view of FIG. 1.

FIG. 2 shows clearly the position of the grooves 10 with respect to the lugs 7.

Figure 3:
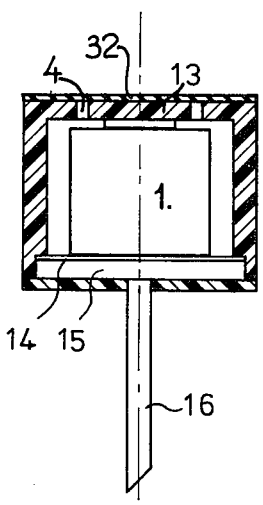
FIG. 3 shows a view in section of a transducer in accordance with a second embodiment, adapted to measure directly the cerebral liquid pressure, without the intermediary of the dura mater.

In the embodiment shown in FIG. 3, a capsule 13 of the transducer contains a magnet 1 and is closed by a membrane 14, similar to the diaphragm 5, and located in a compartment 15 provided with a tubular needle 16. In use, this needle traverses the dura meter and allows the cerebral liquid to flow under its own pressure into the compartment 15, where it exerts a hydrostatic force on the magnet 1 without interference from the dura mater. The behaviour of the transducers of FIGS. 1 and 3 is thus identical.

Figure 6:
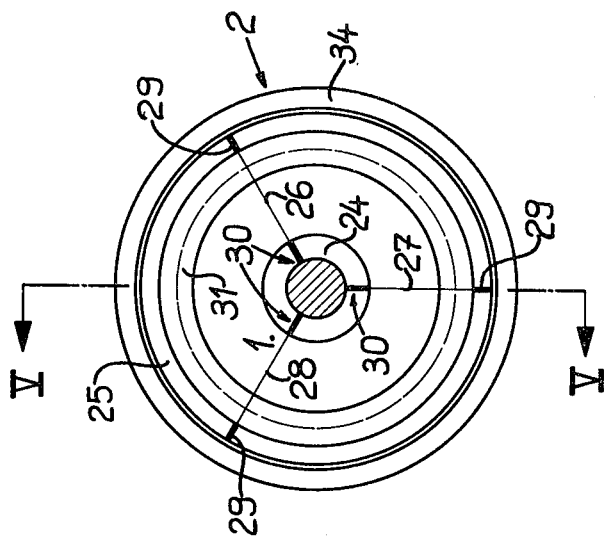
FIG. 6 shows transverse sectional view along the line VI—VI of FIG. 5.
Figure 5:
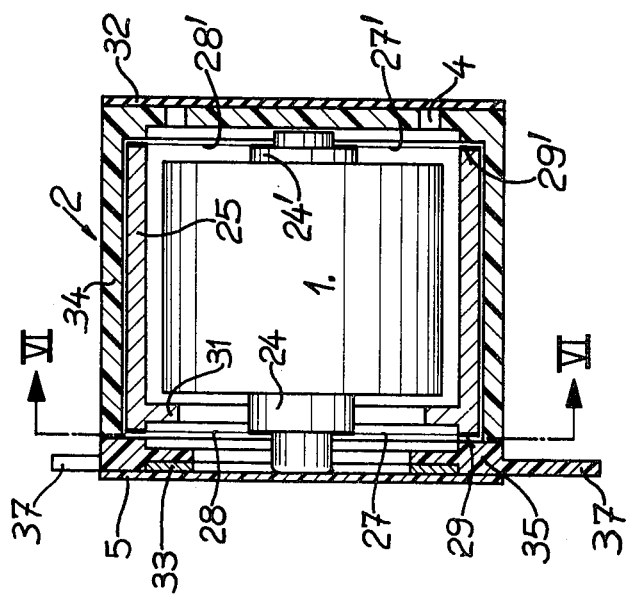
FIG. 5 shows an axial sectional view along the line V—V of FIG. 6 of a transducer in accordance with a third embodiment.

In the case of the transducer of FIGS. 5 and 6, the magnet is guided by elastic filament suspensions 26,27,28 and 26', 27', 28', respectively of high mechanical strength, arranged on two planes perpendicular to the axis of the magnet, in the vicinity of its poles. The filaments may be piano wire.

These filaments are fixed at 30 to the magnet by means of auxiliary rings 24 and 24' respectively, and to an outer envelope 25 at points 29 and 29' respectively.

Small axial displacements of the magnet take place freely, but movements in any other direction are precluded. The amplitude of the axial movement of the magnet is limited by a collar 31 forming part of the envelope 25.

This elastic suspension system, as in the example in accordance with FIGS. 1 and 2, is enclosed in a capsule consisting of two parts 34 and 35 soldered or stuck together, provided with fixing lugs 37 and having its operating face closed by the elastic diaphragm 5. The capsule can be of synthetic material. At 32 there is a semi-permeable film of silicone rubber which permits the transfer via the holes 4 to the interior of the transducer of variations in atmospheric pressure, without permitting liquids to enter.

The magnet of an implanted transducer is submitted at its end turned towards the dura mater, to a hydrostatic force proportional to the intercranial pressure.

Interrogation of the transducer is obtained by submitting it to a magnetic field along its axis, the field being generated by an external inductor.

In a first form, the said inductor generates a purely alternating magnetic field, for example at a power line frequency. Since this field varies rapidly, the magnet is alternately submitted to a force of the same direction as the intercranial hydrostatic force, which tends to maintain it at the base of its capsule, and to a force opposed to the hydrostatic force, which tends to move it from the base of the capsule. When this repulsive force becomes greater than the hydrostatic force, the magnet oscillates audibly.

The intercranial pressure is determined by the relation between this excitation current in the inductor and to the said pressure, which can be determined experimentally.

In a second form, the said inductor generates a direct magnetic field repelling the magnet of the transducer, this direct field being modulated by a small alternating field. When the repulsive magnetic force balances the hydrostatic force, the magnet oscillates under the effect of the small alternating component of the magnetic field of the inductor.

The intercranial pressure is determined from that direct excitation current of the inductor which produces maximum oscillation of the magnet of the transducer.

In a further embodiment, and referring to FIG. 5, the direct and alternating components of the inductor field can be so regulated that the magnet oscillates lightly between the abutments constituted by the base of the capsule 2 and the collar 31. This condition is easily controlled by audible means or by means of an oscilloscope, and permits a very precise adjustment of the direct component of the current, which represents the cranial pressure.

A third alternative consists in submitting the magnet 1 of the transducer to a "pre-restraint", i.e. a static force directed towards the operating face (dura mater side). In its resting position, the magnet 1 bears on a forward abutment constituted by the collar 31. In this rest position the magnet lightly touches the elastic diaphragm 5.

This "pre-restraint", is generated by a ferromagnetic ring 33, fixed to the capsule 2 at one end of the magnet 1, so as to draw it towards the diaphragm 5 with a force opposed to the hydrostatic force generated by the intercranial pressure.

The interrogation of the transducer is effected by the application of the method of embodiment 2 above. The alternating component of the magnetic inductor field generates an audible vibration of the magnet against the collar 31. This vibration is maximum when all the direct forces are balanced, i.e. the hydrostatic force, the pre-restraint and the induced magnetic force.

If the pre-restraint balances a hydrostatic force corresponding to an intercranial pressure of 20 cm of water, for example, the induced force will be in the same direction as the hydrostatic force for the measurement of intercranial pressures less than 20 cm of water, whilst it will be in the opposite direction for the measurement of intercranial pressures greater than 20 cm of water.

An inductor usually has few ampere turns, and is of small dimensions.

A second advantage results from the possibility of using the inductor to measure the "pre-restraint" on the magnet in the implanted position. The direct component of the magnetic inductor field is, to this end, polarised to attract the magnet 1 towards the base of the capsule 2. When approaching this position, the alternating component of the magnetic inductor field produces an audible rattle of the magnet against the base of the capsule 2 which permits calibration of the direct component of the magnetic inductor field, except that the magnet is no longer in contact with the diaphragm acted upon by the hydrostatic force.

Figure 4:
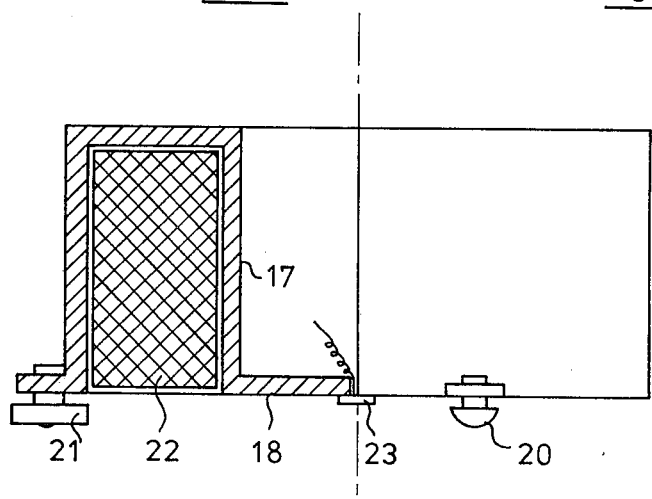
FIG. 4 shows in semi-axial section a magnetic induction generator for reading the transducer.

FIG. 4 gives a mid-sectional view of one form of inductor. The core 17, having a symmetrical surface of revolution, is open on its lower face and is hollowed out and may contain a noise detector of acoustic or electronic type. The core 17 and coil 22 jointly comprise a magnetic circuit. During a measurement, the inductor must be perfectly aligned on the transducer and at a predetermined distance therefrom. The effect of an error in position is inversely proportioned to the diameter of the plane face 18 of the core, so that a large inductor is preferable. The weight of the inductor can then justify mounting it on a mechanical stand.

As a variant, a magnetic field detector 23, enables the position and the distance of the transducer to be accurately ascertained.

Here the inductor is provided with three adjustable feet 20 which rest on the cranium of the patient. One of these feet 21 may include a microphone for the detection of magnet noise.

The magnetic field of the inductor is generated by current applied to the coil 22.

Various methods may be provided to read the variations of the intercranial pressure.

In a first method the intercranial pressure is derived from the noise from the magnet, when subjected to an alternating inductor field of appropriate constant amplitude.

In a second method the intercranial pressure is derived from correlation between a modulation of the inductor field, preferably of saw-tooth form, and the onset of noise from the magnet.

The life expectancy, in the implanted state, of a pressure transducer of the invention is practically unlimited and its output is constant. It measures with sufficient precision the intercranial excess pressure with respect to the ambient atmospheric pressure, without material connection with the atmosphere and consequently without risk of infection and for a moderate price.

The invention is not limited to the embodiments described but extends to all variations thereof, within the scope of the appended claims. For example the elastic suspension systems constituted by the filaments 26, 27, 28 and 26', 27', 28' respectively can be replaced by two metallic diaphragms.

I claim:

1. An intercranial pressure transducer of the passive type, including: a sealed capsule adapted to be housed in the thickness of a skull; a movable permanent magnet within said capsule; guide means for guiding displacement of said magnet axially within said capsule; and said capsule including means for subjecting said magnet to a hydrostatic force generated by the intercranial pressure within said skull, whereby said magnet is displaceable by an external magnetic field applied thereto and which is sufficiently strong to overcome said hydrostatic force applied to said magnet and whereby the strength of the external magnetic field required to displace said magnet is a measure of said intercranial pressure.

2. A transducer as recited in claim 1 wherein said magnet is hollow cylindrical, has its magnetic axis coincident with its geometrical axis, and said guide means guides said hollow cylindrical magnet for displacement along its axis.

3. A transducer as recited in claim 1 wherein said means for subjecting said magnet to a hydrostatic force comprises a water-tight elastic diaphragm defining one end of said capsule which when in use comes into contact with the dura mater of the skull.

4. A transducer as recited in claim 3 wherein said means for subjecting said magnet to a hydrostatic force further includes a compartment exterior to said elastic diaphragm and a tube connected to said exterior compartment for providing communication with the exterior of said capsule, whereby liquid in the skull subject to said intercranial pressure fills said exterior compartment.

5. A transducer as recited in claim 1 wherein said guide means is a rod passing through said magnet.

6. A transducer as recited in claim 1 wherein said guide means are two elastic systems respectively situated in two planes one at each end of said magnet and perpendicular to the magnetic axis thereof, each system being fixed to said magnet and to an outer envelope housed in said capsule such that said suspension device permits small axial displacements of said magnet but opposes its transverse displacement.

7. A transducer as recited in claim 1 including magnet displacement limiting means, comprising a first abutment adjacent an interior face of said capsule and a second abutment opposite said first abutment, for limiting displacement of said magnet.

8. A transducer as recited in claim 7, including means for subjecting said magnet to a pre-restraint force directed towards said means for subjecting said magnet to a hydrostatic force such that said magnet in its rest position in the absence of intercranial pressure is in contact with the first of the said abutments and touches said means for subjecting said magnet to a hydrostatic force.

9. A transducer as recited in claim 8, including a ferromagnetic mass fixed to said capsule near said means for subjecting said magnet to a hydrostatic force to generate said pre-restraint force.

10. A transducer as recited in claim 1 wherein said capsule is provided with fixing lugs adapted to be located in use between said skull and said dura mater.

* * * * *